United States Patent
Särkelä

(10) Patent No.: US 8,219,187 B2
(45) Date of Patent: Jul. 10, 2012

(54) METHOD AND APPARATUS FOR PROVIDING IMPROVED ASSESSMENT OF A PHYSIOLOGICAL CONDITION OF A PATIENT

(75) Inventor: Mika Särkelä, Helsinki (FI)

(73) Assignee: Instrumentarium Corporation, Helsinki (FI)

( * ) Notice: Subject to any disclaimer, the term of this patent is extended or adjusted under 35 U.S.C. 154(b) by 1406 days.

(21) Appl. No.: 11/044,616

(22) Filed: Jan. 27, 2005

(65) Prior Publication Data

US 2006/0167368 A1 Jul. 27, 2006

(51) Int. Cl.
A61B 5/04 (2006.01)

(52) U.S. Cl. ....................................... 600/544
(58) Field of Classification Search ............... 600/544
See application file for complete search history.

(56) References Cited

U.S. PATENT DOCUMENTS

| | | | |
|---|---|---|---|
| 6,631,291 B2 | 10/2003 | Viertiö-Oja et al. | |
| 6,731,975 B1 * | 5/2004 | Viertiö-Oja et al. | 600/544 |
| 6,801,803 B2 | 10/2004 | Viertiö-Oja | |
| 7,215,994 B2 | 5/2007 | Huiku | |
| 7,228,169 B2 | 6/2007 | Viertio-Oja et al. | |
| 2004/0204656 A1 * | 10/2004 | Tolvanen-Laakso et al. | 600/544 |

FOREIGN PATENT DOCUMENTS

WO WO 02/32305 4/2002

OTHER PUBLICATIONS

*Advacing Sedation Assessment to Promote Patient Comfort*, Patricia A. McGaffigan, RN, MS, Critical Care Nurse, Supplement, Career Guide 2002, Feb. 2002, pp. 29-36.

* cited by examiner

*Primary Examiner* — Michael Kahelin
*Assistant Examiner* — Christian Jang
(74) *Attorney, Agent, or Firm* — Andrus, Sceales, Starke & Sawall, LLP

(57) ABSTRACT

In a method and apparatus for providing an indication suitable for assessing a physiological condition of a patient, at least two biosignals are obtained from the patient. The biosignals contain at least one common physiological data component, such as an EEG or EMG component. An analysis of each of the biosignals is carried out to obtain a complexity value for each of the biosignals. Or, the biosignals may be divided into their components and a complexity value is obtained for the biosignal components. Thereafter and on the basis of the complexity values, a complexity value indicative of at least one physiological data component present in the biosignals is selected and utilized to provide the physiological condition assessment indication of the patient.

19 Claims, 3 Drawing Sheets

METHOD AND APPARATUS FOR PROVIDING IMPROVED ASSESSMENT OF A PHYSIOLOGICAL CONDITION OF A PATIENT

FIELD OF THE INVENTION

The present invention relates generally to improving the assessment of a physiological condition of a patient. The invention is primarily intended for monitoring the condition of patients under sedation or anesthesia, although it may also be used in connection with other measurements in which different components contained in biosignals obtained from a patient are relevant to the assessment process.

BACKGROUND OF THE INVENTION

In living organisms, biological processes generate different types of signals, which are generally referred to as biosignals. Biosignals may be is electrical, mechanical or chemical.

Bioelectromagnetism is a broad field including both measurements of electromagnetic fields of bioelectric sources and intrinsic properties of tissue. Measurement of the electromagnetic fields of bioelectric sources covers electricity created in life processes internal in tissues, such as excitation of nerve and muscle tissues. In the measurements of intrinsic properties electric currents are supplied from an external source outside living tissues and electric impedance is monitored. Biosignals may thus refer to either active processes or passive properties of the tissue. However, these passive properties can also be related to electrical or other processes internal in tissues, even though the measurement does not directly utilize the electricity generated internally in tissues.

Neuromonitoring is a subfield of clinical patient monitoring focused on measuring various aspects of brain function including changes caused by drugs commonly used to induce and maintain anesthesia in an operating room or sedation in patients under critical or intensive care.

Electroencephalography (EEG) is a well-established technique for assessing brain activity by recording and analyzing the weak bioelectric signals generated in the cortex of the brain using electrodes attached on the skin of the skull surface. EEG has been in wide use for decades in basic research of the neural systems of the brain as well as in the clinical diagnosis of various neurophysiological diseases and disorders.

Electromyography (EMG) is a method for recording bioelectric signals of muscles. In an EMG measurement, the electrodes are attached on top of a muscle onto the surface of the skin. When an EMG signal is recorded from the forehead of the patient, the recorded signal may include both the activity of the facial muscles (fEMG) and of the brain (EEG). As the frequencies of the EMG spectrum are usually high and above the frequencies of the brain activity, the EMG components can be separated by methods of signal processing or spectral analysis from the EEG signal.

Most patients being cared for in an intensive care unit receive some form of sedation. However, the control of the depth of the sedation administered to a patient is still problematic, and therefore oversedation and undersedation are both common occurrences in ICUs. At present, monitoring the level of sedation is mainly handled by using subjective observations from the patient. Various sedation assessment scales have been developed for subjectively assessing the level of sedation, the Ramsay Score being one of the most widely used tools for this purpose. These scoring systems typically assess the different components of the state of the patient, namely motoric and hypnotic components, and the level of agitation. The scores of the components are, however, not mutually independent and therefore reliable assessment of motoric and hypnotic statuses is difficult or impossible.

However, as discussed in the article by P. A. McGaffigan: Advancing sedation assessment to promote patient comfort, *Critical Care Nurse/Supplement*, February 2002, pp. 29-36, sedation assessment is currently evolving towards a more disciplined and standard part of clinical practice, in which different objective sedation assessment tools are used in order to improve the reliability of the sedation assessment. The need for reliably monitoring the level of sedation is not only based on the desire to improve the quality of the patient care, but also on economy related aspects. As discussed in the above-mentioned article, growing evidence shows that inappropriate sedation can lead to adverse clinical outcomes and reduced efficiencies in critical care settings. Oversedation may cause various complications, such as cardiovascular instability, and it may also increase the length of stay in the hospital and prolong the usage time of expensive facilities, such as the intensive care unit. Undersedation, in turn, may result in patient anxiety and agitation, which can further interfere with care and result in harm to the patient and the nursing staff.

One of the special applications of electroencephalography, which has received attention recently, is the use of a processed EEG signal for objective quantification of the amount of brain activity for the purpose of determining the level of consciousness of a patient. In its simplest form, the utilization of an EEG signal allows for the automatic detection of the alertness of an individual, i.e. if he or she is awake or asleep. This has become an issue of increased interest, both scientifically and commercially, in the context of measuring the depth of unconsciousness induced by anesthesia during surgery. As in the context of sedation, the reasons for the increased interest with respect to anesthesia relate both to the quality of care and to the costs involved. Balanced anesthesia reduces surgical stress and there is firm evidence that adequate analgesia decreases postoperative morbidity. Awareness during surgery with insufficient analgesia may lead to a post-traumatic stress disorder. Low quality pre- and intra-operative analgesia makes it difficult to select the optimal pain management strategy later on. More specifically, it may cause exposure to unwanted side effects during the recovery from the surgery. If the anesthesia is too light and involves insufficient hypnosis, it may cause traumatic experiences both for the patient and for the anesthesia personnel. From an economical point of view, if the anesthesia is too deep, it may cause increased perioperative costs through extra use of drugs and time, and extend the time required for post-operative care.

In connection with anesthesia, the patient is administered hypnotic, analgesic, and neuromuscular blocking agents. The neuromuscular blocking agents block neuromuscular junctions, as a result of which the patient loses the ability to move. Sedatives, in turn, have usually both hypnotic and analgesic properties, but neuromuscular blocking agents are rarely used for sedation.

In addition to EEG signal data, EMG signal data obtained from facial muscles (fEMG) of the forehead is used for monitoring purposes during anesthesia and intensive care. The facial muscles are usually the first indicators of a patient approaching consciousness. When this muscle activity is sensed by appropriately placed electrodes, it provides an early indication that the patient is emerging from anesthesia. Similarly, these electrodes can sense pain reactions when the anesthesia is not adequate due to inadequate analgesia. So, the fEMG signals give an early warning of arousal and may also be indicative of inadequate analgesia.

For defining the level of sedation two different and mutually independent components, namely hypnotic and motoric components, are essential. For assessing the hypnotic state of the patient, EEG signal processing is required, and for assessing the motoric state of the patient, EMG signal processing is normally needed.

An objective tool for assessing the level of anesthesia or sedation is disclosed in International Patent Application WO 02/32305, which describes a method and device for ascertaining the cerebral state of a patient. In this disclosure, a measure derived from EMG signal data enhances and confirms the determination of the hypnotic state made using EEG signal data. As the EMG signal data may be computed more frequently than the EEG signal data, this renders ascertaining changes in the hypnotic state of the patient more rapid. The combined indication provided by the EEG signal data, indicative of the hypnotic component, and EMG signal data, indicative of the motoric component, may also be used for assessing the adequacy of anesthesia or the level of sedation.

Commercially available processes and apparatuses utilizing EEG and EMG signal data for monitoring a patient under sedation or anesthesia rest on a single measurement channel for obtaining the data needed. In other words, the processes utilize the fact that the frequencies of the EMG spectrum are above the frequencies of brain activities, so that the EMG signal component and EEG signal component are obtained from the single channel data by a division of the data.

In order to achieve an accurate measurement of the level of sedation, the indicators indicative of the motoric and hypnotic states should therefore be orthogonal, i.e. mutually independent. However, as the spectra of the EEG and fEMG signals overlap, the discrimination of these two signal components in the single measurement channel requires sophisticated algorithms and optimal electrode position on the forehead of the patient.

The present invention seeks to alleviate or eliminate the above-mentioned drawbacks and to provide a method and apparatus by means of which the accuracy of the measurements may be improved in environments of the above kind, i.e. one in which different biosignal components are relevant in order to obtain a assessment result for a physiological condition of a patient.

SUMMARY OF THE INVENTION

The present invention seeks to provide a method and apparatus for improving the accuracy of patient condition assessment when different biosignal components are relevant to the measurement process. The invention further seeks to provide an approach that is not as sensitive to the positioning of the patient electrodes or current techniques.

In particular, the present invention seeks to improve physiological condition measurement when the condition of a patient under sedation or anesthesia is being monitored.

More specifically, the present invention is directed to an improved method and apparatus for providing such a physiological condition assessment indication that employs a multichannel input, the multichannel input including at least two bioelectromagnetic signals, referred to herein as biosignals, obtained from the patient. The biosignals obtained from the patient will each typically include at least two different signal components, such as an EEG signal component and an EMG signal component. Each of the obtained biosignals of the multichannel input is then subjected to an analysis that determines the complexity of the biosignal. In general, the complexity of an electrical signal is an indication of its unpredictability or randomness. A commonly used complexity determination is the entropy of the signal as expressed in its spectral entropy or approximate entropy.

Using the complexity characteristics of the signals, a selection is made of a complexity value to be used as an indication of each of the biosignal components, for example, the EEG and EMG signal components. These complexity values are then used to provide a physiological condition assessment indication for the patient.

In the above-described manner, each signal component needed in the process obtains the most appropriate representation and overlapping frequency ranges of the components may easily be accommodated.

The number of the input biosignals may vary depending on the measurement process in question. The number of signal components needed for the monitoring of the level of sedation or anesthesia is typically two, although it is to be understood that the invention is not so limited. One or more of the components of the biosignals may also be undesired or possess undesirable characteristics, such as artifacts, in which case the method of the invention serves to determine the biosignals that are least affected by undesired features.

Other features and advantages of the invention will become apparent by reference to the following detailed description and accompanying drawings.

BRIEF DESCRIPTION OF THE DRAWINGS

In the following, the invention and its preferred embodiments are described more fully with reference to the examples shown in the figures of the appended drawing, wherein.

DETAILED DESCRIPTION OF THE INVENTION

Below, the invention is described as used in connection with monitoring the state of a patient under sedation or anesthesia. The invention employs multichannel signal data obtained from the patient. Multichannel signal data here refers to a plurality of separate biosignals measured from the patient. The signal data from the biosignals may be collected in a conventional manner by converting the corresponding analog biosignals received from patient electrodes into digital format and storing the digital signals for further processing.

Each biosignal typically includes a plurality of different biosignal components, such as EEG and EMG components, needed for the monitoring of the patient. The processing of the digitized signals typically uses sets of sequential signal samples representing finite blocks of time, commonly termed "epochs".

Figure 1:
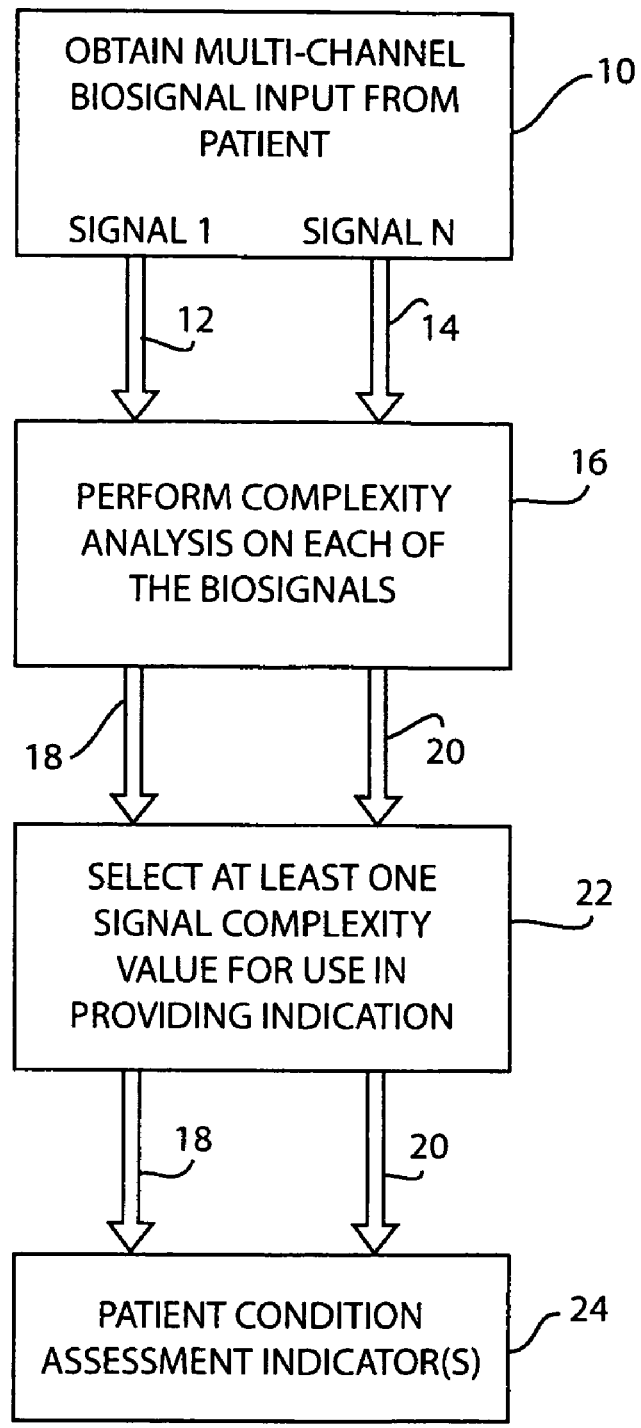
FIG. 1 is a flow diagram showing a generalized embodiment of the method of the present invention.
Figure 3:
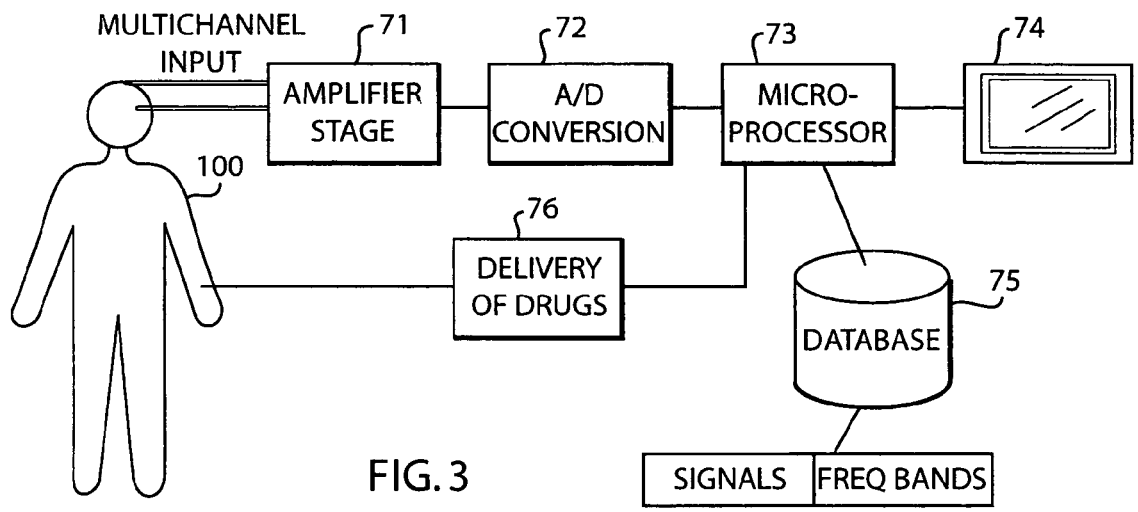
FIG. 3 shows apparatus according to the present invention.

The multichannel input comprised of input signals 1-N shown in FIG. 1, is obtained, in step 10, from electrodes placed on patient 100 shown in FIG. 3. Typically, at least one set of the electrodes is placed on the forehead of the patient and at least one set of electrodes is placed on the scalp of the patient. In the general embodiment of the invention shown in FIG. 1, input biosignals 12 and 14 are obtained. As noted above, each of the biosignals will typically include at least one common biosignal component and typically will include at least two biosignal components, such as an EEG signal component and an EMG signal component. The biosignal 12 may be obtained from the electrodes placed on the scalp of the patient and for this reason will have a significant EEG signal component. The biosignal 14 may be obtained from the electrodes placed on the forehead of the patient and will have a significant EMG signal component.

In step 16, a complexity analysis is performed on each of the biosignals 12 and 14 to obtain a complexity value for each of the biosignals. As noted above and in published PCT Application WO 02/32305 and published U.S. Patent Application 2003/0167019, in general, the complexity of an electrical signal is an indication of its unpredictability, randomness, or disorder.

Currently, the use of spectral entropy is deemed advantageous as an indication of complexity due to the computational simplicity as compared to the other techniques available. However, other quantifications, such as approximate entropy, fractal spectrum analysis, or Lempel-Ziv complexity may also be used for this purpose. As a more detailed discussion of the various mathematical techniques available for obtaining such a quantity can be found in the above-referred patent applications, these methods are not discussed in detail in this context.

In a typical embodiment of the invention, the biosignal from electrodes applied to the scalp of patient 100 to obtain an EEG biosignal will usually have a lower complexity value than that from electrodes applied to the forehead of the patient to obtain an EMG biosignal. This is because an EEG biosignal tends to have a lower degree of disorder than an EMG biosignal.

Step 16 provides complexity values 18 and 20. In step 22 at least one of the complexity values 18 or 20 is selected as a patient condition assessment indicator 24. In a preferred embodiment of the invention, both complexity values 18 and 20 will be combined in a appropriate manner to produce a single, combined indicator parameter or index 24 that includes both the hypnotic and motoric aspects of sedation and/or anesthesia. For example, indicator 24 may be formed as the weighted sum of the two complexity values. The indication may comprise a value that can be compared to a linear scale to provide an objective assessment of the physiological condition of patient 100, for example, the state of anesthesia or sedation of patient 100.

It is also possible that the production of the indication involves presenting the component specific indicators 18 and 20 to the clinician so that the clinician may assess their relative magnitudes. Thus, two columns of information may be displayed to the clinician, the height of the first column indicating the value of the EEG signal component complexity and the height of the second column indicating the value of the EMG signal component complexity. The clinician can then evaluate the state of the patient based on the total and relative heights of the columns.

Figure 2:
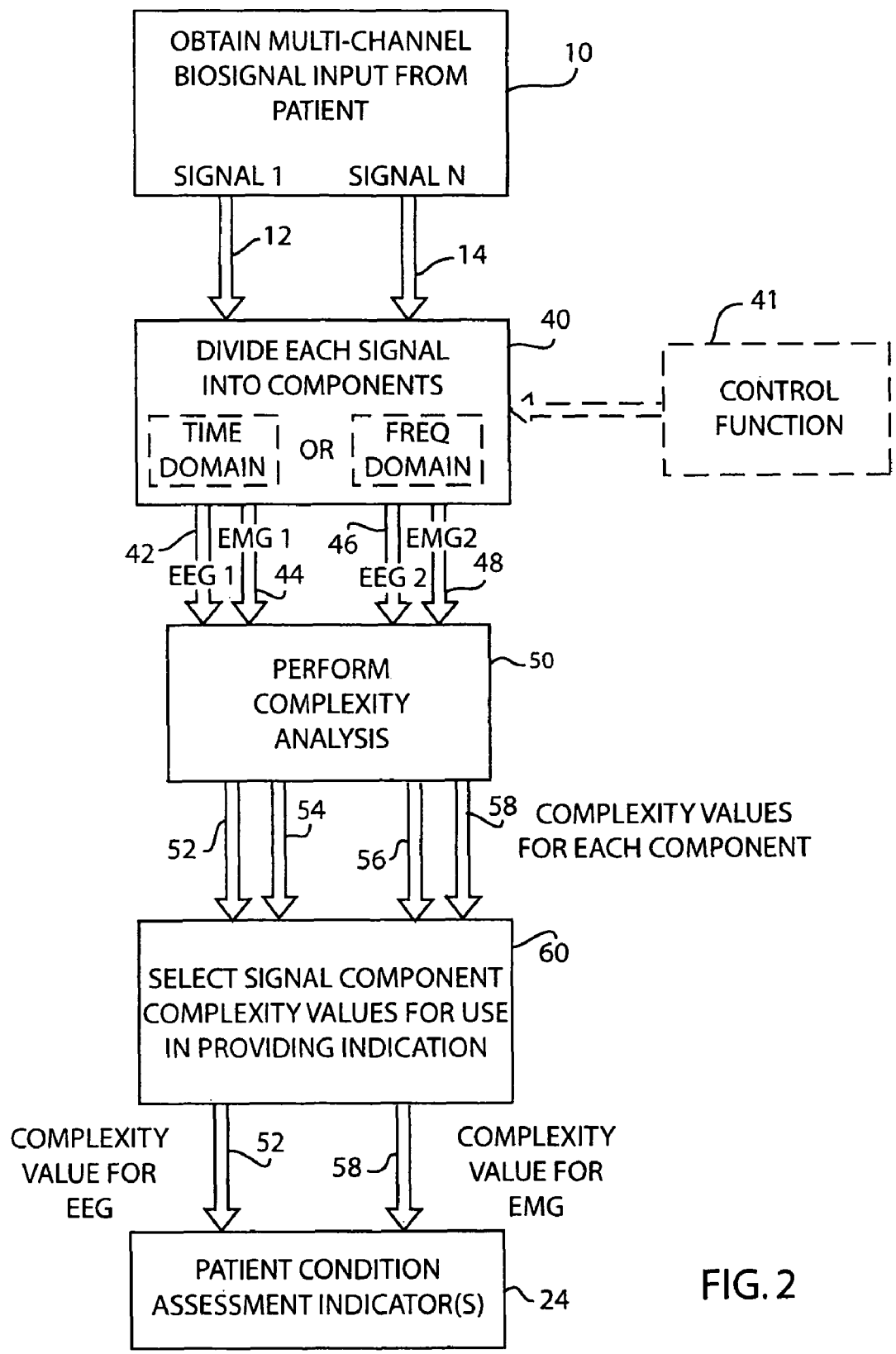
FIG. 2 is a flow diagram showing a modification of the method of the present invention.

FIG. 2 shows a modification of the method shown in FIG. 1. As in the method of FIG. 1, in the method shown in FIG. 2 a multi-channel input is obtained from electrodes applied to patient 100. Thereafter, each of the biosignals obtained in step 10 is divided into its components at step 40. As shown in FIG. 2, this may be carried out on a time domain basis, as by bandpass filtering, or on a frequency domain basis, as by subjecting the obtained signals to a Fourier transform. The division of the biosignals into components may be accomplished by establishing selection bands, for example a lower frequency band for the EEG signal component and a higher frequency band for the EMG signal components. The EEG frequency band may range from 1 Hz up to about 40 Hz and the EMG frequency band from about 20 Hz up to about 80 Hz. In FIG. 2, each input biosignal is shown as divided into two components, a lower frequency component comprising mainly EEG signal data and a higher frequency component comprising mainly EMG signal data to provide component signals 42, 44, 46, and 48.

The characteristics of the signal division occurring in step 40 may be altered, if desired, by control function 41 to, for example, change the bandpass filtering ranges used for signal division.

A complexity analysis is carried out on the components 42-48 of the obtained signals at step 50 to provide the complexity value 52, 54, 56, and 58 for each component signal.

Thereafter, a selection of the signal component complexity values to be used to form patient condition assessment indicator 24 is carried out at step 60. As noted above in connection with the embodiment of the invention shown in FIG. 1, it is desirable to provide an indicator 24 that is representative of both the hypnotic and motoric aspects of the patient's condition. To this end, a one of the complexity values 52-58 having a lower complexity value will be usually selected to represent the EEG component inasmuch as the low complexity value indicates that this component has a smaller amount of EMG signal data and hence a larger amount of EEG signal data. Similarly, a one of the complexity values 52-58 having a higher complexity value will be selected to represent the EMG component inasmuch as the high complexity value indicates that this component has a smaller amount of EEG signal data and hence a larger amount of EMG signal data. For exemplary purposes, FIG. 2 shows complexity value 52 as representing the EEG component and complexity value 58 as representing the EMG component.

The selected complexity values are then combined and/or presented in the same manner as described in connection with FIG. 1 to provide patient condition assessment indicator 24.

As the steps of the method are repeated to monitor the physiological condition of the patient, it will be appreciated that the biosignal that is used to obtain the EEG complexity value and the biosignal that is used to obtain the EMG complexity value may differ from epoch to epoch as the properties of the biosignals obtained from the patient in the multi-channel input change.

Also, in the process, signals that are most affected by signal phenomena, termed artifacts, not directly related to the signal data used to determine the state of sedation or depth of anesthesia of a patient, may be eliminated. Such spurious signals may, for example, be those arising from the respiration or cardiac functioning of the patient, electrosurgery or defibrillation, or eye movements. Thus, for example, in a frequency domain based signal division in step 40, out of several biosignals from 1 to N, the one that is least affected by an artifact may be selected, such as the biosignal having the lowest spectral power in a band in which frequencies relating to the respiratory functioning of the patient is found. Or, step 60 may be used to lessen the effects of artifacts in providing indicator 24, since high frequency noise will increase the complexity value of a signal and low frequency noise will decrease the complexity value and the selection process may take these circumstances into account. Other artifact techniques may also be used to reject signals from further processing in the method of the present invention.

FIG. 3 illustrates an embodiment of apparatus according to the invention for providing an improved patient condition assessment indicator. The multichannel input signal data is obtained from one or more sensors attached to a patient 100. The sensors are ordinarily electrodes applied to the scalp and forehead of patient 100. The input biosignals are supplied to an amplifier stage 71, that amplifies the signals before they are sampled and converted into digitized format in an A/D converter 72. The digitized signals are then supplied to a microprocessor 73 which may carry out artifact detection and rejection, for example.

Microprocessor 73 is provided with a database or memory unit 75 holding the digitized signal data obtained from the sensors. The database may further hold the parameters needed for the above-described operation, such as the frequency bands corresponding to each signal component, or reference values, if comparison to reference values is used in the division of biosignals and/or selection of the biosignal complexity.

The microprocessor 73 carries out the signal division, complexity determination, and signal selection steps shown in FIGS. 1 and 2, and provides patient condition assessment indicator 24.

When a patient under sedation is monitored, the microprocessor displays the above described patient condition assessment indicator on the screen of a monitor 74 connected to the microprocessor. The composite indication may be displayed in various ways using graphical and/or numeric or textual information. The microprocessor may further supply the determined indicators as input data to a device or system 76 delivering drugs, such as anesthetic agents, to the patient.

As is obvious from the above, the method and apparatus of the invention is not sensitive to the positioning of the electrodes on the patient, since the system is able to select the biosignal that is the best representative for each signal component needed.

Although the invention was described above with reference to the examples shown in the appended drawings, it is also obvious that the invention is not limited to these, but may be modified by those skilled in the art without departing from the scope and spirit of the invention.

What is claimed is:

1. A method for providing an indication suitable for assessing a physiological condition of a patient, said method comprising the steps of:
    (a) obtaining two biosignals from the patient, each biosignal being obtained from a different location on the patient, the biosignals each containing an EEG signal component and an EMG signal component;
    (b) dividing each of the two obtained biosignals into the EEG signal component and the EMG signal component in a microprocessor;
    (c) carrying out an analysis of both the EEG signal component and the EMG signal component of the two biosignals in the microprocessor to obtain a complexity value for both the EEG signal component and the EMG signal component of the two biosignals;
    (d) selecting, on the basis of the complexity values, the lower complexity value of the EEG signal components for use as an indication of the EEG signal component and selecting the higher complexity value of the EMG signal components for use as an indication of the EMG signal component; and
    (e) utilizing the selected complexity values in the microprocessor to provide a physiological condition assessment indication of the patient.

2. The method of claim 1 wherein the obtained complexity values are the entropies of the biosignals.

3. The method of claim 2 wherein the obtained complexity values are the spectral entropies of the biosignals.

4. The method of claim 2 wherein the obtained complexity values are the approximate entropies of the biosignals.

5. The method of claim 1 wherein the obtained complexity values are the Lempel-Ziv complexities of the biosignals.

6. The method of claim 1 wherein the obtained complexity values are obtained from fractal spectrum analysis of the biosignals.

7. The method of claim 1 wherein the step of dividing the biosignals is carried out on a time domain basis.

8. The method of claim 1 wherein the step of dividing the biosignals is carried out on a frequency domain basis.

9. The method of claim 1 where a criterion used to divide the biosignals into components is changeable.

10. The method of claim 1 wherein steps (b), (c), and (d) are periodically repeated.

11. The method of claim 1 or 10 further defined as a method for assessing the state of sedation or anesthesia of a patient.

12. The method of claim 1 or 10 further defined as using the indication provided in step (d) to control the delivery of drugs to the patient.

13. A method for providing an indication suitable for assessing a physiological condition of a patient, said method comprising the steps of:
    (a) obtaining two biosignals from the patient, each biosignal being obtained from a different location on the patient, the biosignals each containing an EEG signal component;
    (b) carrying out an analysis of each of the two biosignals in a microprocessor to obtain a complexity value for each of the two biosignals;
    (c) utilizing the microprocessor to select, on the basis of the complexity values, the lower complexity value for use as an indication of the EEG signal; and
    (d) utilizing the selected complexity value in the microprocessor to provide a physiological condition assessment indication of the patient.

14. The method of claim 13 wherein the obtained complexity values are the entropies of the biosignals.

15. The method of claim 14 wherein the obtained complexity values are the spectral entropies of the biosignals.

16. The method of claim 14 wherein the obtained complexity values are the approximate entropies of the biosignals.

17. The method of claim 13 wherein the obtained complexity values are the Lempel-Ziv complexities of the biosignals.

18. The method of claim 13 wherein the obtained complexity values are obtained from fractal spectrum analysis of the biosignals.

19. The method of claim 13 wherein steps (b), (c), and (d) are periodically repeated.

* * * * *